United States Patent
Jain et al.

(10) Patent No.: US 10,702,234 B2
(45) Date of Patent: Jul. 7, 2020

(54) IMAGE COMBINING USING IMAGES WITH DIFFERENT FOCAL-SPOT SIZES

(71) Applicant: CANON MEDICAL SYSTEMS CORPORATION, Otawara-shi (JP)

(72) Inventors: Amit Jain, Amherst, NY (US); Joseph Manak, Albany, NY (US); Haruki Iwai, Toyonaka (JP)

(73) Assignee: CANON MEDICAL SYSTEMS CORPORATION, Otawara-shi (JP)

( * ) Notice: Subject to any disclaimer, the term of this patent is extended or adjusted under 35 U.S.C. 154(b) by 610 days.

(21) Appl. No.: 15/439,657

(22) Filed: Feb. 22, 2017

(65) Prior Publication Data

US 2018/0235564 A1  Aug. 23, 2018

(51) Int. Cl.
*A61B 6/00* (2006.01)
*A61B 6/03* (2006.01)
*A61B 6/06* (2006.01)

(52) U.S. Cl.
CPC .......... *A61B 6/5235* (2013.01); *A61B 6/405* (2013.01); *A61B 6/482* (2013.01); *A61B 6/50* (2013.01); *A61B 6/5258* (2013.01); *A61B 6/032* (2013.01); *A61B 6/06* (2013.01); *A61B 6/5205* (2013.01)

(58) Field of Classification Search
CPC .............................. A61B 6/405; A61B 6/5235
See application file for complete search history.

(56) References Cited

FOREIGN PATENT DOCUMENTS

| DE | 42 30 880 A1 | | 3/1994 | |
|---|---|---|---|---|
| DE | 195 04 305 A1 | | 8/1996 | |
| WO | WO 2010 018480 A1 | | 2/2010 | |
| WO | WO-2010018480 A1 | * | 2/2010 | ........... A61B 6/5229 |

* cited by examiner

*Primary Examiner* — Dani Fox
(74) *Attorney, Agent, or Firm* — Oblon, McClelland, Maier & Neustadt, L.L.P.

(57) ABSTRACT

A method and apparatus is provided to generate two X-ray projection images, using different focal-spot sizes in the X-ray source. The large and small focal-spot images have different image qualities (e.g., different signal-to-noise rations (SNR) and different resolution). The two images are combined, in either the spatial or frequency domains, to generate a combined image, exhibiting the best attributes of the constitutive small and large focal-spot images. In the spatial domain, change regions and uniform regions are determined based on spatial variations within the images, and the superposition generating the combined image weights the small focal-spot image more in the change regions and the large focal-spot image more in the uniform regions. In the frequency domain, the combined image superimposes low-frequency components of the large focal-spot image with high-frequency components of the small focal-spot image.

21 Claims, 12 Drawing Sheets

Lookup Table (LUT)

| FS | kVp | mAs | Kernel |
|---|---|---|---|
| $FS_1$ | $kVp_1$ | $mAs_1$ | $K_{111}$ |
| $FS_1$ | $kVp_1$ | $mAs_2$ | $K_{112}$ |
| $FS_1$ | $kVp_1$ | $mAs_3$ | $K_{113}$ |
| $FS_1$ | $kVp_2$ | $mAs_1$ | $K_{121}$ |
| $FS_1$ | $kVp_2$ | $mAs_2$ | $K_{122}$ |
| $FS_1$ | $kVp_2$ | $mAs_3$ | $K_{123}$ |
| $FS_1$ | $kVp_3$ | $mAs_1$ | $K_{131}$ |
| $FS_1$ | $kVp_3$ | $mAs_2$ | $K_{132}$ |
| $FS_1$ | $kVp_3$ | $mAs_3$ | $K_{133}$ |
| $FS_2$ | $kVp_1$ | $mAs_1$ | $K_{211}$ |
| $FS_2$ | $kVp_1$ | $mAs_2$ | $K_{212}$ |
| $FS_2$ | $kVp_1$ | $mAs_3$ | $K_{213}$ |
| $FS_2$ | $kVp_2$ | $mAs_1$ | $K_{221}$ |
| $FS_2$ | $kVp_2$ | $mAs_2$ | $K_{222}$ |
| $FS_2$ | $kVp_2$ | $mAs_3$ | $K_{223}$ |
| $FS_2$ | $kVp_3$ | $mAs_1$ | $K_{231}$ |
| $FS_2$ | $kVp_3$ | $mAs_2$ | $K_{232}$ |
| $FS_2$ | $kVp_3$ | $mAs_3$ | $K_{233}$ |
| $FS_3$ | $kVp_1$ | $mAs_1$ | $K_{311}$ |
| $FS_3$ | $kVp_1$ | $mAs_2$ | $K_{312}$ |
| $FS_3$ | $kVp_1$ | $mAs_3$ | $K_{313}$ |
| $FS_3$ | $kVp_2$ | $mAs_1$ | $K_{321}$ |
| $FS_3$ | $kVp_2$ | $mAs_2$ | $K_{322}$ |
| $FS_3$ | $kVp_2$ | $mAs_3$ | $K_{323}$ |
| $FS_3$ | $kVp_3$ | $mAs_1$ | $K_{331}$ |
| $FS_3$ | $kVp_3$ | $mAs_2$ | $K_{332}$ |
| $FS_3$ | $kVp_3$ | $mAs_3$ | $K_{333}$ |

IMAGE COMBINING USING IMAGES WITH
DIFFERENT FOCAL-SPOT SIZES

FIELD

This disclosure relates to a method and apparatus for combining X-ray projection images alternately generated using an X-ray source operating with two or more different focal-spot sizes, and, more particularly, to combining the images with two or more than two focal spot sizes to achieve a better signal-to-noise ratio (SNR) than the small focal-spot image and a better resolution than the large focal-spot image.

BACKGROUND

Radiography systems and methods are widely used, particularly for medical imaging and diagnosis. Radiography systems generally create two-dimensional projection images through a subject's body. A radiation source, such as an X-ray tube, irradiates the body from one side. A collimator, generally adjacent to the X-ray source, limits the angular extent of the X-ray beam, so that radiation impinging on the body is substantially confined to a cone-beam/fan-beam region (i.e., an X-ray projection volume) defining an image volume of the body. At least one detector on the opposite side of the body receives radiation transmitted through the body substantially in the projection volume. The attenuation of the radiation that has passed through the body is measured by processing electrical signals received from the detector.

X-ray projection images having high spatial resolution are desirable in order to visualize fine details in the image. However, spatial resolution can be limited by the detector pixel size. Additionally, the spatial resolution can be limited by the spatial extent of the X-ray source (i.e., the focal spot size), and the geometrical arrangement among the source, the imaged object, and the X-ray detector. The short wavelength of X-rays minimizes the effects of diffraction. However, as the size and spacing of the pixels of the X-ray detector array continue to get smaller with improvements in detector technology, improvements to decreasing the size of the focal-spot size in X-ray sources have failed to keep pace, resulting in the X-ray source being the limiting factor in resolution. Due to intrinsic material and thermal constraints in X-ray tubes, the focal spot size has remained relatively constant, whereas the critical dimensions of the X-ray detector array (e.g. the width and spacing of the detector elements in the array) have decreased over time, until now the spatial resolution for X-ray detects is smaller than the width of the point-spread function of X-ray sources operating under typical clinical settings.

The focal spot is the point where the electron beam strikes a target within an X-ray tube. Thus, the focal-spot size is determined by the size of the electron beam and the aspect angle between the surface struck by the X-rays and the direction from the X-ray source to the target. A small focal-spot size improves the resolution of the X-ray imaging, resulting in more detailed images. However, it is often difficult to use a small focal-spot size due to the constraints imposed by X-ray tube loading necessary to achieve a desired exposure and signal-to-noise-ratio (SNR).

The width of the focal spot is not the only factor determining the point-spread function. Additionally, the point-spread function is affected by the ratio between object-imager distance (OID) and source-imager distance (SID). The closer an object is to the detector and the farther away the object is from the source, the smaller the point-spread function becomes, resulting in less blurring in the generated image. Thus, the spatial resolution can be improved by making the ratio SID:OID large. This can be accomplished by keeping the OID to a minimum, e.g., by keeping the object close to the detector. Further, the ratio SID:OID is large when the SID is large by positioning the object a long distance from the X-ray source. However, practical constraints impose bounds on how large the ratio SID:OID can be for clinical applications.

In clinical X-ray imaging systems, the focal-spot size is typically on the order of one millimeter, which is large enough to be the limiting factor for the X-ray image resolution. High resolution detectors with a pixel size significantly less than one millimeter create potential for higher resolution X-ray imaging, but this potential cannot be fully realized without overcoming the practical limitations imposed by the size of focal spots and magnification factors. Tube design limitations present obstacles to improve X-ray imaging resolution without degrading the SNR by decreasing the exposure. A method of increasing resolution without significantly degrading SNR in X-ray images would be advantageous.

The "background" description provided herein is for the purpose of generally presenting the context of the disclosure. Work of the presently named inventors, to the extent it is described in this background section, as well as aspects of the description which may not otherwise qualify as conventional art at the time of filing, are neither expressly nor implicitly admitted as conventional art against the present disclosure.

BRIEF DESCRIPTION OF THE DRAWINGS

A more complete understanding of the disclosure is provided by reference to the following detailed description when considered in connection with the accompanying drawings, wherein:

FIG. 12 is an exemplary look-up table, according to one embodiment.

DETAILED DESCRIPTION

Practical constraints limit the smallest focal-spot size for X-ray tubes used as X-ray sources for projective imaging, and this limit to the focal-spot size in turn limits the resolution achievable in such applications as radiography, computed tomography, fluoroscopy, and angiography. These constraints include practical size limitations, heat transfer and material characteristics, dose constraints (e.g., maintaining the radiation dosage as low as reasonably possible), and time constraints. As a practical matter, a larger focal-spot size can generate a greater flux of X-rays resulting in a higher signal-to-noise ratio (SNR) in the projection images, but the larger focal-spot size comes at the cost a poorer spatial resolution. The methods and apparatus described herein combine the best of large and small focal-spot sizes by acquiring projection images using both a large and a small focal-spot sizes, and the before fusing the projection images into a single image that has both good spatial resolution similar to an image generated using a small focal-spot size and larger SNR similar to an image generated using a large focal-spot size. The importance of achieving good spatial resolution is becoming more significant as X-ray detector sizes continue to decrease.

Figure 1A:
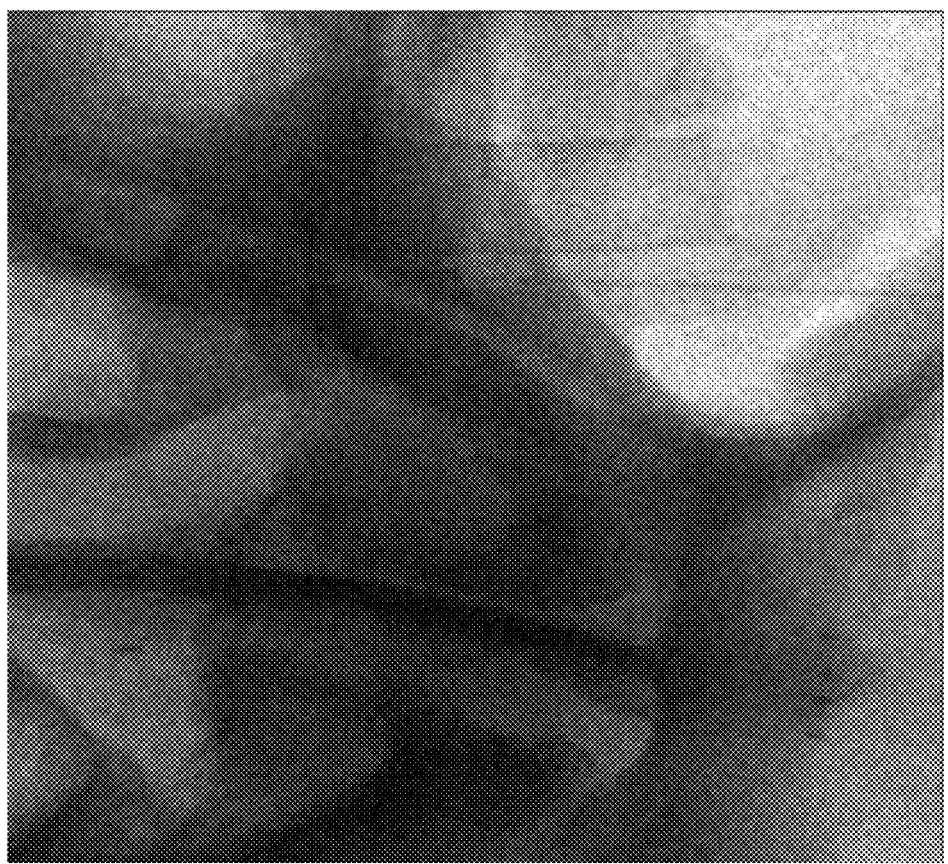
FIG. 1A is a projection image generated using a small focal spot and a relatively small X-ray exposure.
Figure 1B:
FIG. 1B is a projection image generated using a focal spot that is larger than the focal spot used to obtain FIG. 1A and the exposure is twice as large as in FIG. 1A.

Referring now to the drawings, wherein like reference numerals designate identical or corresponding parts throughout the several views, FIGS. 1A and 1B show two projection images taken using different focal-spot sizes. FIG. 1A shows an X-ray projection image acquired using a smaller focal-spot size than the focal-spot size used to acquire the X-ray projection image shown in FIG. 1B. The focal spot in FIG. 1A is smaller than in FIG. 1B, and the X-ray exposure from FIG. 1B is twice as larger as in FIG. 1A. Higher resolution is visible in FIG. 1A than in FIG. 1B, but FIG. 1A sacrifices SNR in order to obtain this improved resolution. This is because the X-ray flux achievable using the smaller focal-spot size is less, resulting in smaller signals and thus lower SNRs in FIG. 1A compared to FIG. 1B.

Thus, it can be observed that focal-spot sizes, such as those used for the existing clinical systems, which are significantly large relative to the critical detector dimension adversely impact the overall system resolution. While the focal-spot size depends on particular design choices and trade-offs for a given X-ray imager, generally, the focal spot for all X-ray imagers is on the order of one millimeter due to the tube loading capacity for smaller focal spots. Ideally, the focal-spot size would be made arbitrarily small, but that cannot be achieved due to X-ray tube design limitations. Ultimately, there is a trade-off between resolution and image quality. On the one hand, a larger focal-spot size can provide more exposure and greater SNR, but this greater SNR comes at the expense of poorer spatial resolution. On the other hand, smaller focal-spot sizes improve spatial resolution, but this improvement comes at the expense of less exposure and a smaller SNR.

To obviate the challenges of this trade-off, the methods described herein combine together a small focal-spot size X-ray image with a large focal-spot size X-ray image to achieve a combined image having both better SNR and better resolution than achievable using only a single X-ray image. That is, the methods described herein take advantage of the comparative benefits of both large and small focal spots to have images that combine the best aspects of both types of images. In these methods, a large focal spot image can be obtained with a larger SNR, and a small focal spot image can be obtained with a finer resolution. Then, the large and small focal-spot images can be combined to have the resolution of the small focal-spot image and the SNR of the large focal-spot image.

For example, in certain implementations, the methods described herein combines the small focal-spot image with the large focal-spot image by selecting sub-images from within the respective images to be combined together to generate a combined sub-image.

Further, these methods can be applied to computed tomography (CT) data. For example, CT projection data from a CT scan is made up of a series of projection images each corresponding to a different projection angle. In contrast to conventional CT, for each projection angle, two X-ray projection images can be acquired corresponding respectively to a large focal-spot image and a small focal-spot image. Then the methods described herein for combining the large focal-spot image with the small focal-spot image can be performed for each projection angle to generate respective combined projection images for each projection angle, and a reconstructed image can be generated from the combined projection images.

Alternatively, the large focal-spot images can be used to reconstruct a reconstructed large focal-spot image, and the small focal-spot image can be used to reconstruct a reconstructed small focal-spot image. Then, the large and small focal-spot reconstructed images can be combined using the methods described herein.

As will be described, the combining of small and large focal-spot images can be performed in either the spatial domain or spatial-frequency domain.

As mentioned above, the methods described herein have several advantages over more conventional methods. First, combining multiple images together to leverage the best qualities of each respective image type increases the flexibility for optimizing among various X-ray imaging parameters—not just focal-spot size. This flexibility can extend to other X-ray parameters, including: the voltage difference from the anode to the cathode (i.e., the kVp), the current, the duration of the imaging window, and the choice of beam filter. Thus, many potential combinations are available to obtain a combination of images that can generate an optimal image quality, according to some predefined image-quality metric. Second, the methods described herein are advantageous when used with X-ray detectors having small pixel sizes to improve spatial resolution, as discussed above. Third, in certain implementations, the methods described herein can improve image quality without resorting to a higher dose of radiation to a patient. For example, the use of a larger focal spot for normal exposure to achieve low noise/high SNR together with a smaller focal-spot to achieve higher resolution images can be achieved without a higher radiation dose to the patient. Fourth, to achieve even higher image quality, the methods described herein can be combined with various denoising methods and/or iterative reconstruction (IR) CT techniques that use edge-preserving regularizers to improve image quality and resolution.

Figure 2:
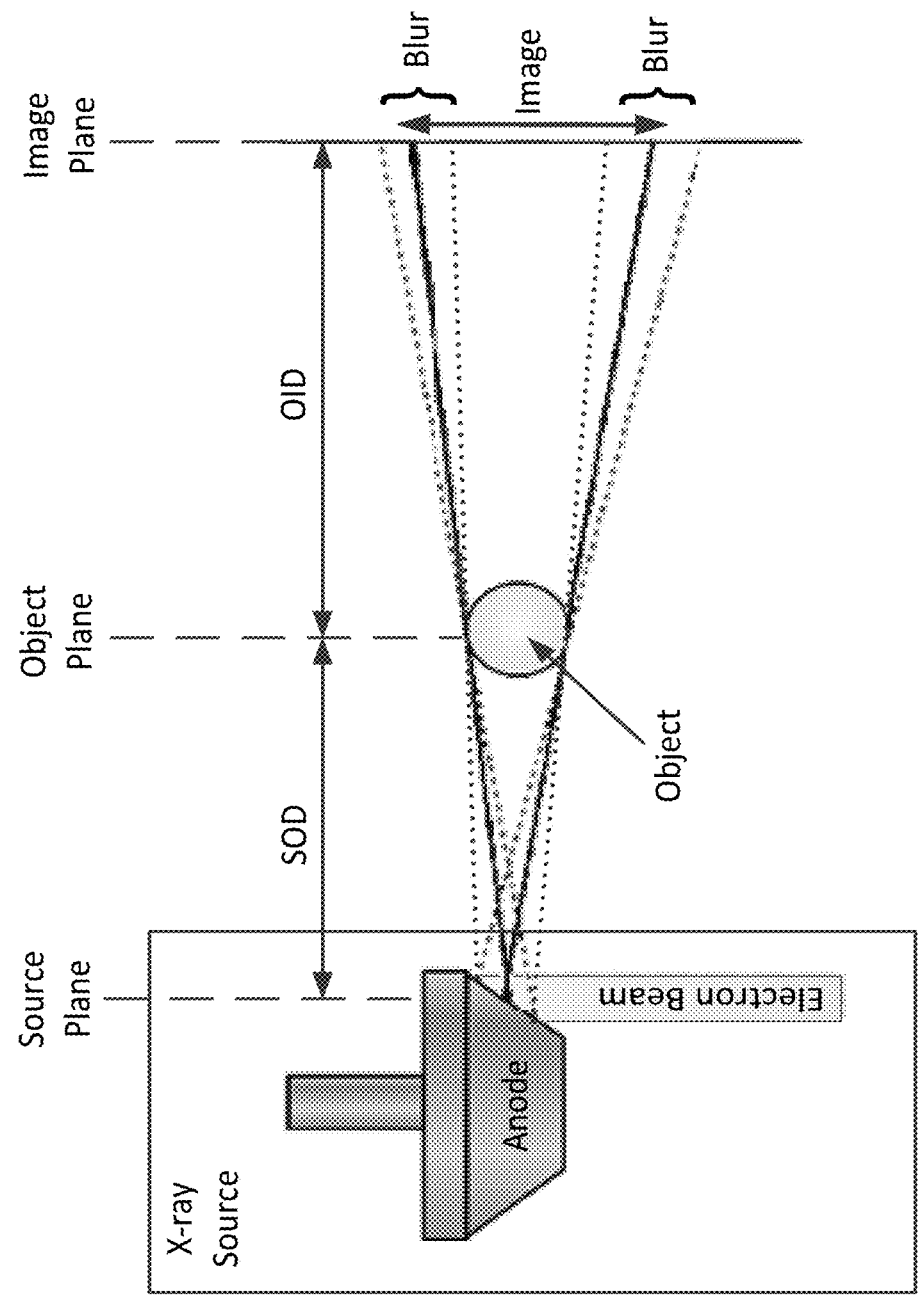
FIG. 2 shows a diagram of blurring in an X-ray projection image resulting from a finite width of a focal spot in the X-ray source.

FIG. 2 illustrates an exemplary imaging system in which an object is imaged by X-rays from an X-ray source passing through the object being detected at an image plane. The size of the electron beam on the anode of the X-ray source determines the focal-spot size. The solid lines show the ray trajectories from a center of the focal spot and passing through the periphery of the object. The dashed lines show the X-ray trajectories for X-rays from the edges of the focal spot passing through the periphery of the object. When the source-to-object distance (SOD) is much greater than the object-to-imaged distance (OID), the magnification is small and the point-spread function in the image plane is reduced. The magnification and the point-spread function of the image at the image plane can also be affected by the use an X-ray filter/lens (e.g., a butterfly filter) at the source. The relationship between the geometry of the X-ray apparatus and the focal-spot size to the image resolution and point-spread function are generally well understood and can be modeled using straightforward ray tracing, and, therefore, these details are not discussed herein.

Figure 3:
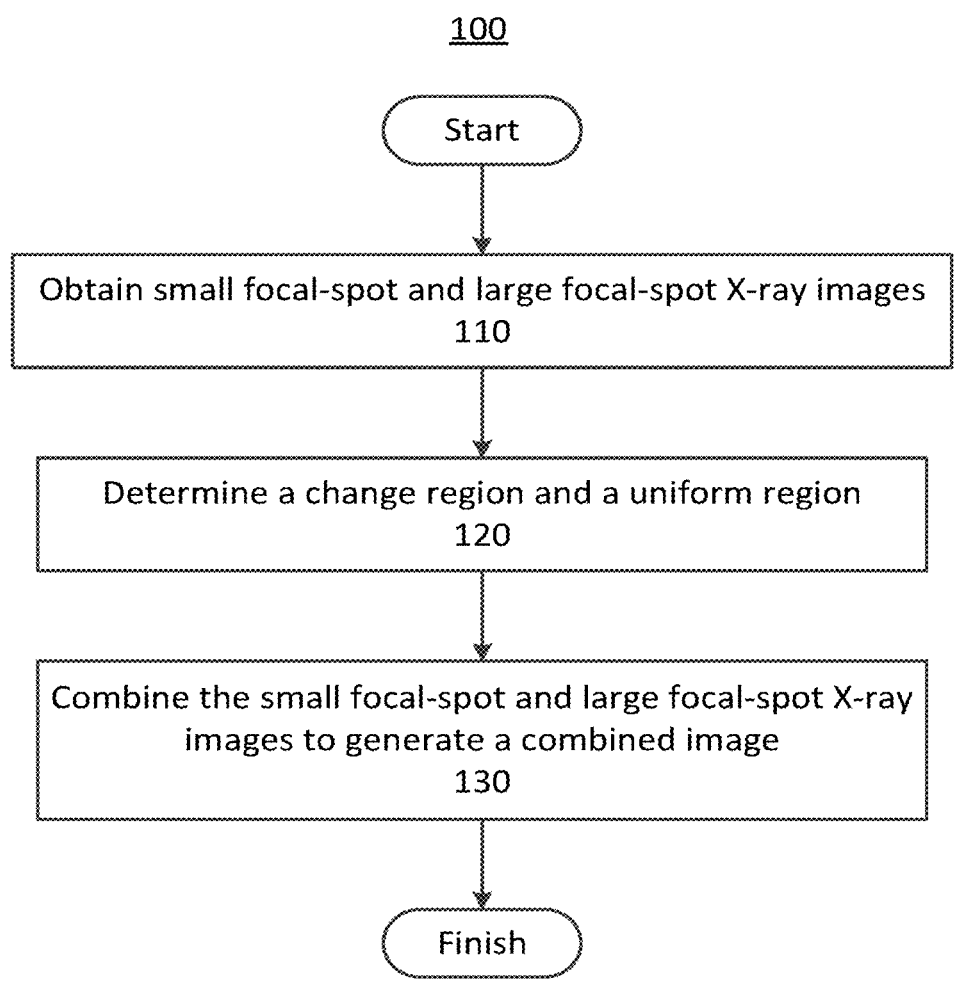
FIG. 3 shows a flow diagram of a method of combining small and large focal-spot images in a spatial domain, according to one embodiment.

FIG. 3 shows a flow diagram of a method 100 for combining small and large focal-spot images.

In step 110 of method 100, two projection images are obtained using two different focal-spot sizes. These images can be obtained either by making a projection measurement using an X-ray imager, or by recalling from a computer memory projection data that was previously acquired. To make a projection measurement, an X-ray source directs X-rays toward an object, and, after passing through the object, the X-rays are detected using an X-ray film or an array of X-ray detector elements. For example, the X-ray detector array can detect pixel values that make up the projection image, and the distance between adjacent pixels in the detector array is the minimum resolution of the projection image.

By taking the ratio between projection images with and without the object in the X-ray path, the X-ray absorption through the object can be determined as a logarithm of the ratio between the measured X-ray intensities. As mentioned above, in step 110, attenuation/projection images are obtained using two different focal-spot sizes. The first attenuation/projection image corresponds to the X-ray source using a large focal-spot size at the anode of the X-ray source, and the second attenuation/projection image corresponds to the X-ray source using a small focal-spot size at the anode of the X-ray source. Generally, compared to the large focal-spot image, the small focal-spot image will have finer resolution due to the smaller focal-spot size, but will also have smaller SNR due to the lower total X-ray flux that can be generated from a smaller focal-spot size, as discussed above.

In step 120 of method 100, image processing is used to determine regions of uniform X-ray absorption within the projection images and regions exhibiting large spatial variations in the X-ray absorption.

For example, the point-spread function for the large focal-spot image will be wider than the point-spread function for the small focal-spot image. Assuming that the detector elements are linear, the respective images for the small and large focal-spot sizes are equivalent to a convolution between a perfect resolution image (i.e., an image having a delta-function as its point-spread function) and the corresponding point-spread functions, which can be determined from the respective focal spots and the relative positions of the components of the X-ray imaging system, as discussed above. Thus, a difference between the small and large focal-spot projection images is equivalent to the convolution between the perfect-resolution image and a difference point-spread function, which is a difference between the large focal-spot point-spread function and the small focal-spot point-spread function. Based on this insight, the changes regions can be determined by taking a difference between the two projection images to generate a difference image, and then taking the cross-correlation between the difference image and the difference point-spread function, which functions as a matched filter for detection. Regions where the cross-correlation is large will correspond to large spatial variations in the measured attenuation, whereas a small cross-correlation value indicates a region of mostly uniform attenuation.

For example, regions of large variation can be found at the boundaries between organs, whereas regions within an organ can exhibit a high degree of uniformity. Further, regions of rapid variation can be found where a stent or other external device has been implanted in a patient, where the external device presents a region of either greater or lesser attenuation than the surrounding organs and tissue. In certain implementations, the cross-correlation can be locally normalized by dividing the cross-correlation value by an average of the local attenuation. For example, the average of the local attenuation can be obtained by low-pass filtering one of the small and large focal-spot images to represent an averaged local attenuation.

In certain implementations, other methods of detecting uniform regions and change regions can be used. For example, an edge detection method can be used to detect change regions, in which case the uniform regions can be identified as those regions in which edges are not detected and change regions surround detected edges. Additionally, wavelet transformations can be used to detect edges. Also, a measure of the mean-normalized variance or frequency content (e.g., mean frequency) within a moving window can be used to determine regions corresponding to change and uniformity.

In certain implementations, the image space can be divided discretely into regions that are identified as either change regions or uniform regions. In other implementations, each pixel or sub-image comprised of several adjacent pixels within the image can be labeled by a continuous number indicating a percentage to which the pixel/sub-image belongs to a category of either a uniform region or a change region. For example, fuzzy logic can be used to determine the degree to which the various pixels/sub-images belong to the fuzzy sets of uniform and change regions. In certain implementations, a third type of region having properties in between the change regions and the uniform regions can be identified, and, within the images, this third in-between region can provide a buffer between the change and uniform regions.

In step 130 of method 100, the large and small focal-spot images are combined to generate a combined image. For each pixel the combined image will be a linear superposition of the corresponding pixel values from the large and small focal-spot images. For example, the pixel values of the combined image can be given by $$p_{n,m}^{(C)} = w_{n,m} p_{n,m}^{(S)} + (1-w_{n,m}) p_{n,m}^{(L)},$$

wherein $p_{n,m}^{(C)}$ is the pixel value of the $n^{th}$ row and the $m^{th}$ column of the combined image, $p_{n,m}^{(L)}$ and $p_{n,m}^{(S)}$ are respectively the pixel values of the $n^{th}$ row and the $m^{th}$ column of the large and small focal-spot images, and $w_{n,m}$ are the weights indicating the degree to which a pixel is in a change region. In the combined image, those pixels identified to be primarily or entirely within a change region will have weights greater than 0.5, resulting in the pixel values being predominantly derived from the small focal-spot image.

In certain implementations, the weights $w_{n,m}$ can be determined using fuzzy logic.

In certain implementations, the weights $w_{n,m}$ at the transitions demarked by boundaries between change regions and uniform regions (and in certain implementations between/among change regions and uniform regions and in-between regions) can be tapered/smoothed to make the function of the weights $w_{n,m}$ at these transitions mathematically continuous (and in certain implementations mathematically smooth, e.g., the first order derivative is not infinite). For example, the weights $w_{n,m}$ can have a value of one in change regions, zero in uniform regions, and, for regions buffering in between the change and uniform regions, the weights $w_{n,m}$ can be interpolated using a straight-line transition between nearest points on the change region and the uniform region.

In certain implementations, other interpretation functions can be used to determine the weights $w_{n,m}$ in regions in between the change and uniform regions, including spline functions, quadratic or cubic interpolation functions, other polynomial functions, and Gaussian interpolation functions, for example.

In addition to those steps shown in method 100, to improve the image quality, denoising and/or filtering of the various images can be performed at various points with the flow diagram shown in FIG. 3. For example, the large and small focal spot images can be denoised separately before generating the combined image. Additionally, after the combined image is generated the combined image can be denoised and/or filtered. Various denoising methods can be applied to the respective images, including: linear smoothing filters, anisotropic diffusion, non-local means, and non-linear filters.

Linear smoothing filters remove noise by convolving the original image with a mask that represents a low-pass filter or smoothing operation. For example, the Gaussian mask comprises elements determined by a Gaussian function. This convolution brings the value of each pixel into closer agreement with the values of its neighbors. In general, a smoothing filter sets each pixel to the average value, or a weighted average, of itself and its nearby neighbors; the Gaussian filter is just one possible set of weights. Disadvantageously, smoothing filters tend to blur an image because pixel intensity values that are significantly higher or lower than the surrounding neighborhood are smeared or averaged across their neighboring area. Sharp boundaries become fuzzy. Generally, local linear filter methods assume that local neighbourhood are homogeneous, and local linear filter methods, therefore, tend to impose homogeneity on the image obscuring non-homogeneous features, such as lesions or organ boundaries.

Anisotropic diffusion removes noise while preserving sharp edges by evolving an image under a smoothing partial differential equation similar to the heat equation. If the diffusion coefficient were spatially constant, this smoothing would be equivalent to linear Gaussian filtering, but when the diffusion coefficient is anisotropic according to the presence of edges, the noise can be removed without blurring the edges of the image.

A median filter is an example of a nonlinear filter and, if properly designed, a nonlinear filter can also preserve edges and avoid blurring. A median filter operates, for example, by evaluating each pixel in the image, sorting the neighboring pixels according to intensity, and replacing the original value of the pixel with the median value from the ordered list of intensities. The median filter is one example of a rank-conditioned rank-selection (RCRS) filter. For example, median filters and other RCRS filters can be applied to remove salt and pepper noise from an image without introducing significant blurring artifacts.

In addition a filter using a total-variation (TV) minimization regularization term can be used where it is assumed that the areas being imaged are uniform over discrete areas with relatively sharp boundaries between the areas. A TV filter can also be used as another example of a nonlinear filter.

In non-local means filtering, rather than performing a weighted average of pixels according to their spatial proximity, pixels are determined to be a weighted average according to the similarity between patches within the images. Thus, noise is removed based on non-local averaging of all the pixels in an image—not just the neighboring pixels. In particular, the amount of weighting for a pixel is based on the degree of similarity between a small patch centered near that pixel and another small patch centered around the pixel being denoised.

Figure 4:
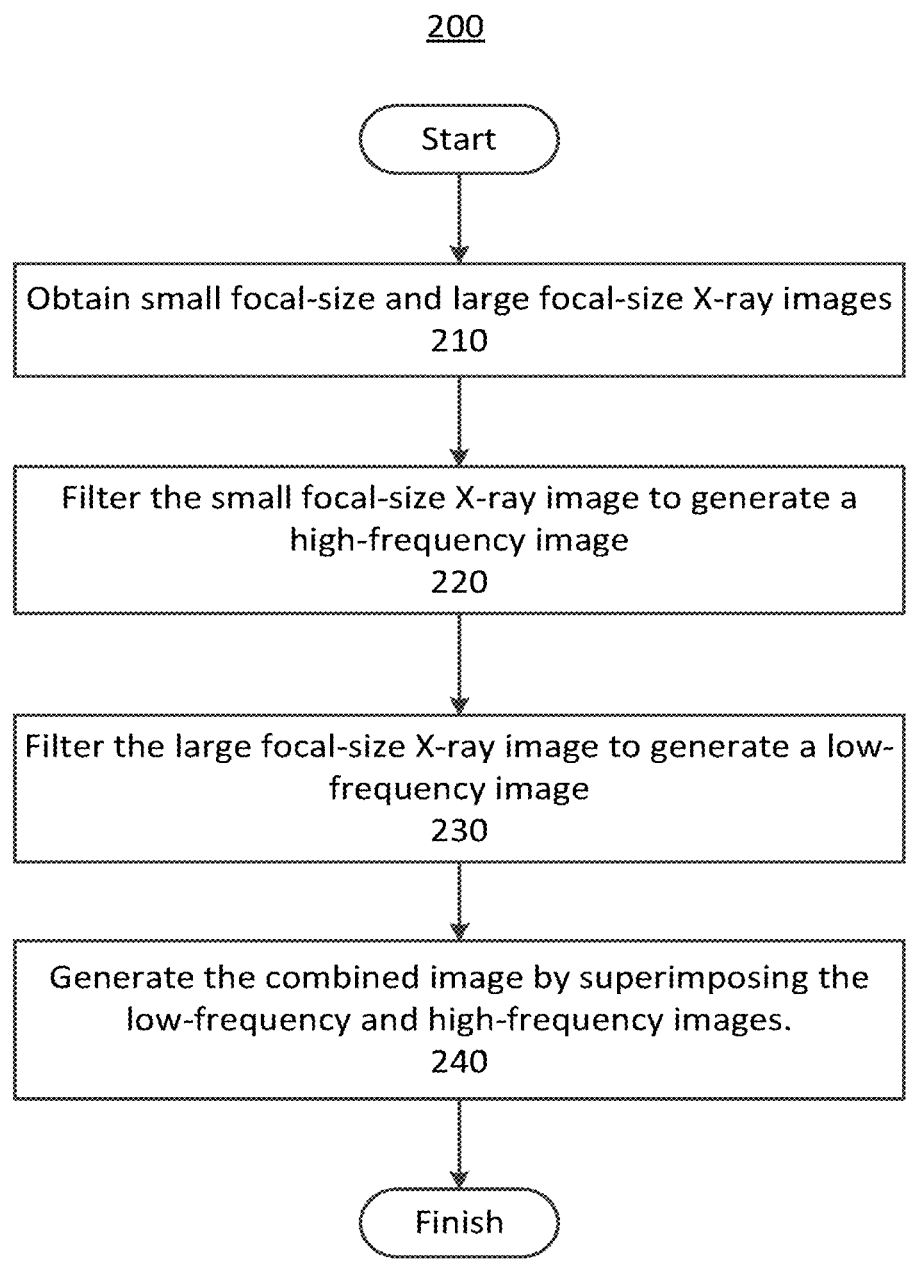
FIG. 4 shows a flow diagram of a method of combining small and large focal-spot images in a frequency domain, according to one embodiment.

FIG. 4 shows a flow diagram of a method 200 of combining small and large focal-spot images. Method 200, in contrast to method 100, combines the small and large focal-spot images in the frequency domain, rather than the spatial domain.

In step 210 of method 200, the small and large focal-spot images are obtained using two different focal-spot sizes, similar to step 110 of method 100.

In step 220 of method 200, a high-frequency image is generated by high-pass filtering or band-pass filtering the small focal-spot image. As discussed above, the small and large focal-spot images are respectively equivalent to a convolution between a perfect resolution image and their respective point-spread functions. Thus, the Fourier transformations of the respective point-spread functions represent effective low-pass, which limits the frequency content of the small and large focal-spot images. The small focal-spot cutoff frequency of the point-spread function of the small focal-spot image will be greater than the large focal-spot cutoff frequency of the point-spread function of the large focal-spot image because the small focal-spot image has better resolution corresponding to higher frequency content. In the small focal-spot image, frequency content above the small focal-spot cutoff frequency will be dominated by noise. Similarly, in the large focal-spot image, frequency content above the large focal-spot cutoff frequency will be dominated by noise. Accordingly, in certain implementations, the high-frequency image is generated by band-pass filtering the small focal-spot image using a band-pass filter having a 3 dB cutoff frequencies corresponding to the small focal-spot cutoff frequency and the large focal-spot cutoff frequency.

In other implementations, the high-frequency image is generated by high-pass filtering the small focal-spot image using a high-pass filter having a 3 dB cutoff frequency corresponding to the small focal-spot cutoff frequency. The high-pass or band-pass filter can be any known filter type including: a Gaussian filter, a Hann filter, a Hamming filter, a Balckman-Harris Filter, a Bartlett-Hann filter, a Tukey filter, a Chebychev filter, and a Dolph-Chebychev filter. Additionally, different implementations can use different cutoff frequencies for the band-pass or high-pass filter.

In step 230 of method 200, a low-frequency image is generated by low-pass filtering the large focal-spot image. For example, the low-pass filter can have a 3 dB cutoff frequency corresponding to the large focal-spot cutoff frequency. Any type of low-pass filter can be used, and different implementations can use different cutoff frequencies for the low-pass filter.

In certain implementations, the generation of the high- and low-frequency images can be generated using a wavelet transformation. The low-frequency image can be generated by selecting low-frequency components of a wavelet transformation of the large focal-spot image, and the high-frequency image can be generated by selecting high-frequency components of a wavelet transformation of the small focal-spot image.

Any known method can be used to generate the high-frequency image from the small focal-spot image and to generate the low-frequency image from the large focal-spot image.

In step 240 of method 200, the low-frequency image and the high-frequency image are combined to generate a combined image. For example, the low-frequency image and the high-frequency image are combined by adding the low-frequency image with the high-frequency image.

Figure 5:
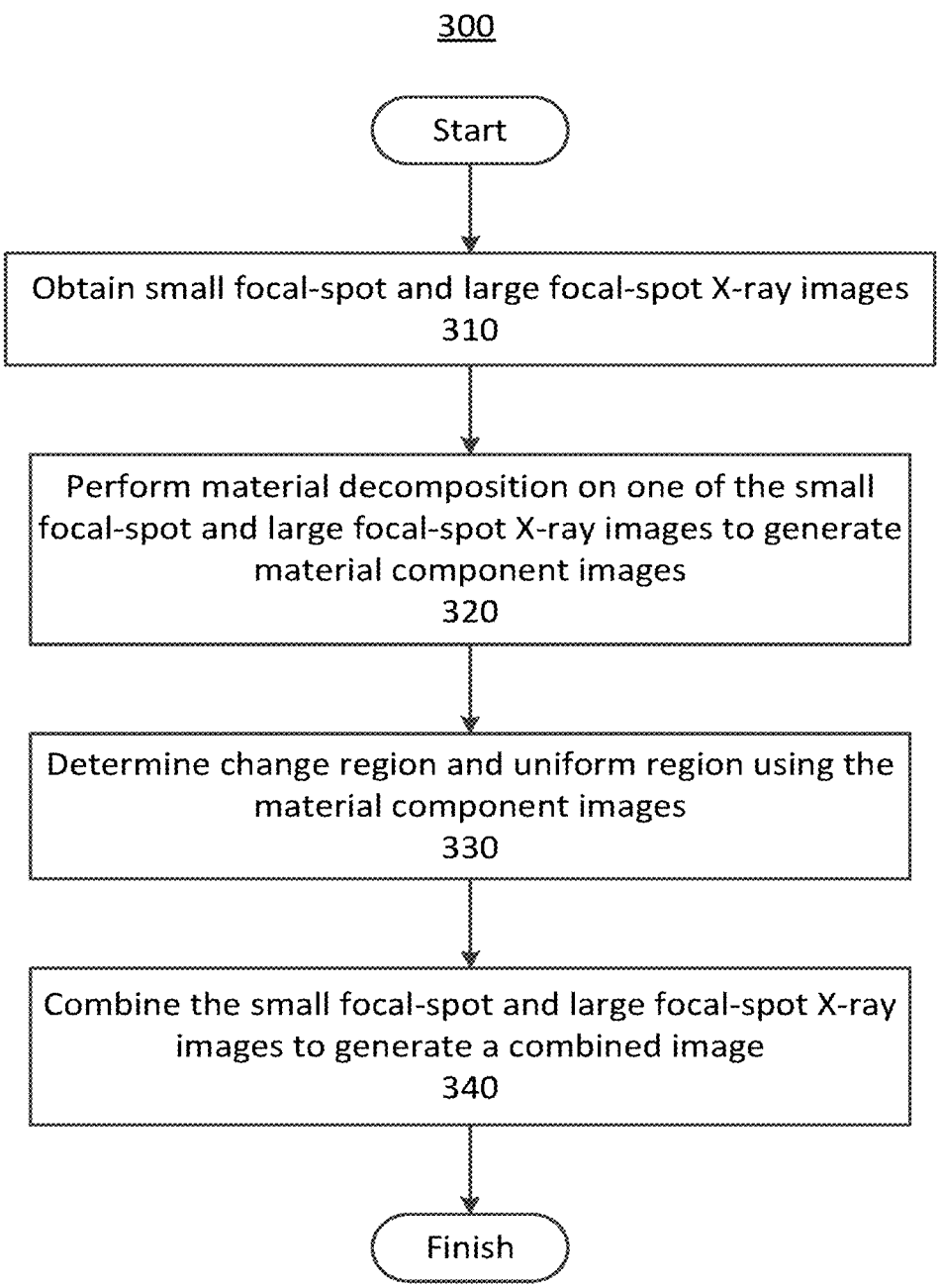
FIG. 5 shows a flow diagram of a method of combining small and large focal-spot images using a material decomposition to identify change regions and uniform regions, according to one embodiment.

FIG. 5 shows a flow diagram of a method 300 of combining small and large focal-spot images. Method 300, like method 100, combines the small and large focal-spot images in the spatial domain.

In step 310 of method 300, the small and large focal-spot images are obtained, similar to step 110 of method 100.

In step 320 of method 300, the small and large focal-spot images are decomposed into material components. This material decomposition can be performed directly on the projection data.

Alternatively, a reconstructed image can be reconstructed from a CT scan, and the material decomposition can be performed on the reconstructed images. Next, the material components of the reconstructed images can be forward projected to generate material components of the small and large focal-spot images.

In certain implementations, the material components can be generated from dual-energy projection measurements or spectrally resolved projection measurements.

In step 330 of method 300, the change regions and the uniform regions can be determined using the material components of the small and large focal-spot images. The change regions and the uniform regions can be determined from the material components using the methods described in step 120 of method 100. Additionally, a change in the ratio between the material components for adjacent and/or proximate pixels/sub-images can be used as a figure of merit indicating a change region.

In step 340 of method 300, the small and large focal-spot size images are combined, as described in step 130 of method 100.

Figure 6:
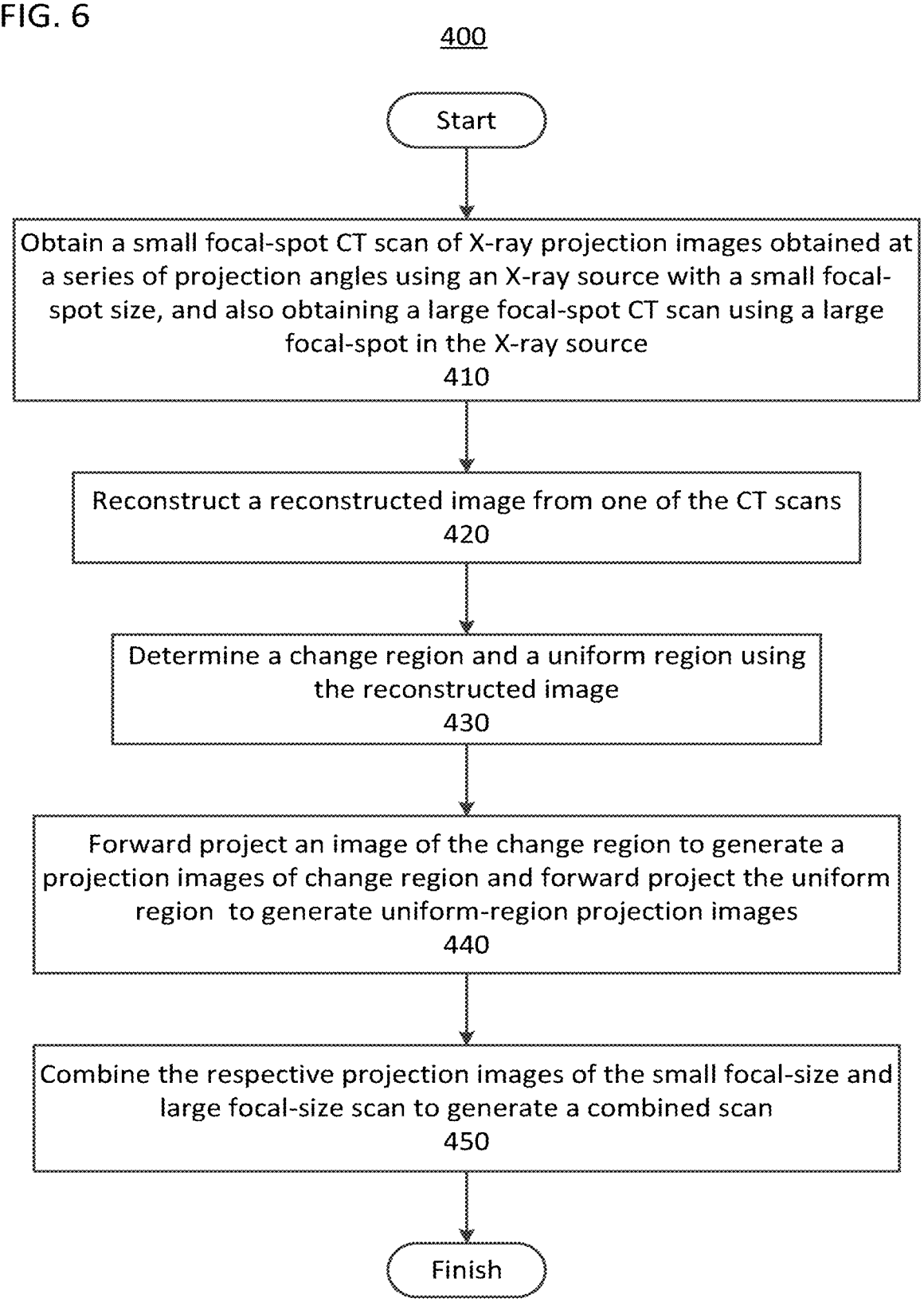
FIG. 6 shows a flow diagram of a method of combining small and large focal-spot computed tomography (CT) scans by reconstructing images of the imaged object to identify change regions and uniform regions, according to one embodiment.

FIG. 6 shows a flow diagram of a method 400 of combining small and large focal-spot images. Method 400, like method 100, combines the small and large focal-spot images in the spatial domain.

In step 410 of method 400, two computed tomography (CT) scans are obtained. These scans can be obtained either by making a series of projection measurement at a series of projection angles using an X-ray CT scanner, or by recalling, from a computer memory, CT scans that were previously acquired. The first projection scan uses a small focal spot and the second projection scan uses a large focal spot. These two scans can be taken by moving to each projection angle and acquiring both a large and a small focal-spot image at the projection angle before rotating to the next projection angle, or by taking an entire CT scan at all of the projection angles using only one focal-spot size before changing the focal-spot size and taking the next CT scan.

In step 420 of method 400, reconstructed images are generated from the large and small focal-spot CT scans. These large and small focal-spot reconstructed images can be generated using filtered back-projection, statistical iterative reconstruction, or any other known method of CT image reconstruction. In certain implementations, iterative reconstruction is advantageous because a regularizer, such as a total-variation (TV) minimization regularizer, can be applied to the iterative reconstruction in order to reduce the noise while maintaining sharp edges and fine detail in the reconstructed images.

In step 430 of method 400, the change and uniform regions are determined using the reconstructed images rather than the projected images. Although the reconstructed images have one more dimension than the projected images (e.g., a three-dimensional reconstructed image can be reconstructed from two-dimension projection data), the methods described above in step 120 of method 100 and step 330 of method 300 for determining change regions and uniform regions within the projection images can also be straight forwardly extended and applied to the reconstructed images. For example, the reconstructed image can be decomposed into material components, and the uniforms and change regions can be determined from the material components, as described in step 330 of method 430.

In certain implementations, an edge-detection method can be used to detect the change regions.

Additionally, in certain implementations, a cross-correlation can be calculated between a difference between the large and small focal-spot reconstructed images and a difference between the large and small focal-spot point-spread functions, and the cross correlation can be compared to a threshold or series of thresholds to classify pixels into change regions and uniform regions (e.g., using a threshold and region growing method).

Further, any combination of change/uniform-region-detection methods described here, in step 120 of method 100, or in step 330 of method 300 can be used to determine the change and uniform regions (and in certain implementations that use in-between regions, the in-between regions can also be determined in the manner described above).

In step 440 of method 400, the change regions and the uniform regions are forward projected to generate projection images of the change regions and the uniform regions. In certain implementations, each volume pixel in a given reconstructed image is assigned a value between zero and one representing whether the volume pixel corresponds to a change region or not. The pixel values of the projection image then represent a line integral through volume pixels.

In certain implementations, a threshold is used to determine which pixel values are sufficiently large to represent change regions, and those pixel values exceeding the threshold are assigned a value of one.

In certain implementations, all values less than the threshold are normalized by the threshold.

In certain implementations, all values less than a second threshold are set to zero, and values between the first threshold on the second threshold are mapped onto a value between zero and one using a monotonic function.

A similar process to those described above can be used for determining the projection images of the uniform regions by forward projecting the reconstructed images of the uniform regions. These examples of determining change regions and uniform regions in the projection images from the change regions and uniform regions in the reconstructed images are provided as illustrations and not by way of limitation. Other methods of generating uniform/change region projection images from the uniform/change region reconstructed images are contemplated as being part of method 400 described herein.

In step 450 of method 400, the small and large focal-spot projection images can be combined, as described in step 130 of method 100 and step 340 of method 300.

In certain implementations, step 440 can be omitted and the small and large focal-spot reconstructed images can be directly combined using the uniform and change regions determined for the reconstructed images and using the methods described in step 130 of method 100 and step 340 of method 300.

In certain implementations, the frequency content of the combined image relative to the frequency content of the small and large focal-spot images can be used to provide feedback to adjust and fine tune the thresholds for the change regions and the uniform regions. For example, if the threshold for the change regions is set too high, regions with high-frequency content can be omitted from the change regions. Then the omitted high-frequency regions will be derived less from the small focal-spot image, which has more high-frequency content, and more from the large focal-spot image, which has less high-frequency content. Because the large focal spot image will contribute more in the omitted regions and the frequency content of the large focal spot image is less than the frequency content of the small focal spot image, the high threshold for the change regions ultimately results in a less high-frequency content in the combined image.

If the combined image were merely an average between the large and small focal-spot images, the frequency content of the combined image would have a mean about halfway between the frequency content of the large and small focal-spot images. If, however, the thresholds are properly chosen, those regions in the combined image with significant high-frequency content are derived predominantly from the small focal-spot image, and the uniform regions, for which the frequency content is nearly identical between the large and small focal-spot images, is derived from large focal-spot image. Thus, for properly chosen change and uniform thresholds, the combined image can have frequency content approaching the frequency content of the small focal-spot image. When the frequency content of the combined image is observed to deviate significantly from the frequency content of the small focal-spot image, then the criteria/threshold for the change regions in likely too strict and should be relaxed and/or the criteria/threshold for the uniform regions in likely too relaxed and should be stricter.

Additionally, the relative areas of the uniform and change regions can be used, in certain implementations, as feedback to assess whether the criteria/thresholds for the change and uniform regions should be revised and fine tuned.

Figure 7A:
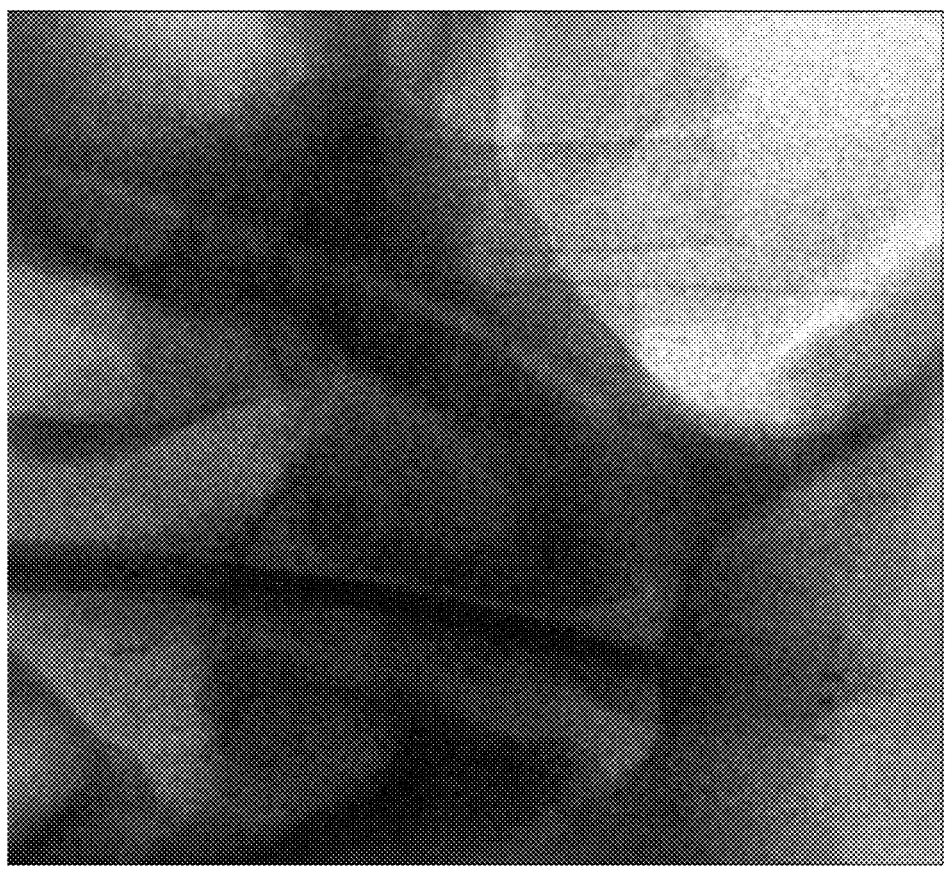
FIG. 7A is a combined image generated using a cross-correlation based image-combining method.

FIG. 7A shows a combined image using the large and small focal-spot images from FIGS. 1A and 1B. The combined image in FIG. 7A was generated using a cross correlation to determine the uniform and change regions. The region with relatively high-frequency contents (e.g. a stent and/or wire) was selected in both the images. To replace the high-frequency region from the large focal spot image by the corresponding high-frequency region from the small focal spot image. Registration was performed between the two images. This registration included that the cropped region from the small focal spot image was obtained and then cross correlation coefficients were generated to find the transformation between the images corresponding to the maximum likelihood. The transformation (e.g., spatial rotations and translations) corresponding to the maximum cross correlation coefficient was use to replace the portion of large focal spot image with cropped image portion from small focal spot image. It can be observed that the changes regions corresponding to boundaries and edges within the image of FIG. 7A are noisier than the uniform regions. This is because the small focal-spot images are noisier than the large focal-spot images and the small focal-spot images are predominantly represented in these change regions.

Figure 7B:
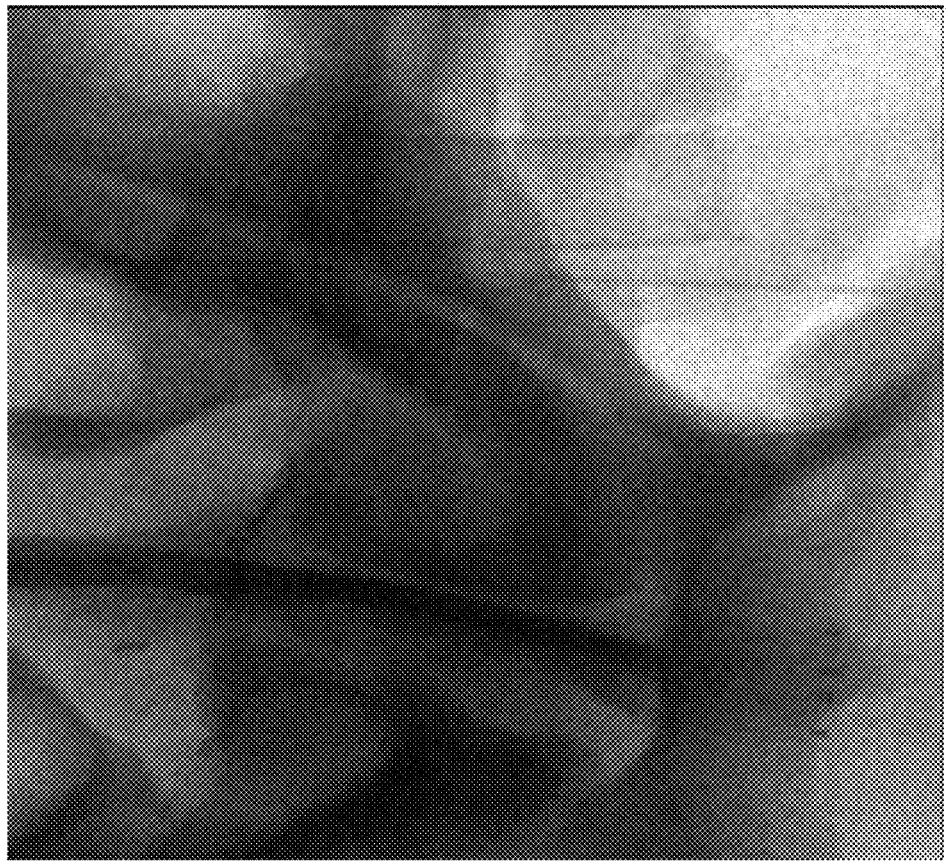
FIG. 7B is a combined image generated using a cross-correlation based image-combining method that minimizes noise by using a different number of images and/or images at different exposures.

FIG. 7B shows a combined image using the large and small focal-spot images from FIGS. 1A and 1B. The extra noise near the boundaries and edges is mitigated in FIG. 7B by using a different number of images and/or images at different exposures. The noise appearance is different in the images taken with small and large focal spot due to difference in exposure. This difference could be minimized with the use of appropriated temporal recursive or spatial temporal filter depending on the variation in the background. For example if there is no significant movement in the background, a recursive temporal filter with higher weight could be used.

Figure 8:
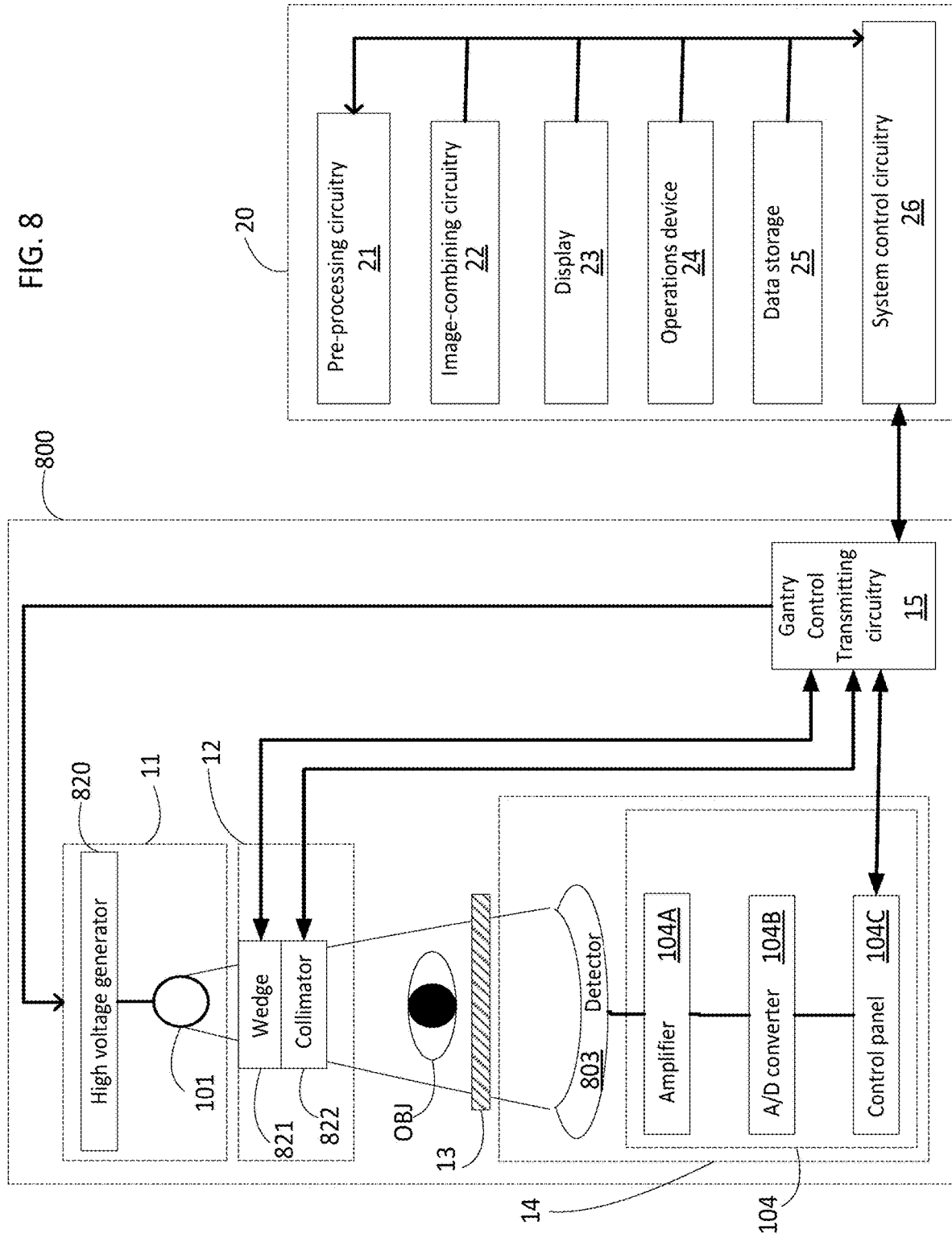
FIG. 8 is a block diagram of an example of a X-ray imaging apparatus, according to one embodiment.

FIG. 8 is a block diagram of an exemplary X-ray apparatus that can be used to perform the methods described herein, e.g., methods 100, 200, 300, and 400. The X-ray apparatus includes a gantry 800 and a console 20. The gantry 800 includes an X-ray system 11, an optical system 12, a patient table 13, a detection system 14, and a gantry control transmission circuitry 15.

The X-ray system 11 includes a high voltage generator 820 and an X-ray tube 101. The high voltage generator 820 applies a high voltage to the X-ray tube 101 under the control of the gantry control transmission circuitry 15, and supplies a filament current to the X-ray tube 101 under the control of the gantry control transmission circuitry 15. The X-ray tube 101 generates X-rays to be applied to an object OBJ upon receiving a high voltage and a filament current from the high voltage generator 820.

The collimation system 12 includes a filter/attenuator 821 which cuts soft X-rays of X-rays generated from the X-ray tube 101 and adjusts the intensity distribution of the X-rays. A collimator 822 opens and closes in accordance with a field size at the time of a radiograph. The collimation system 12 forms an X-ray beam with an optimized exposure dose and irradiates the object OBJ with X-rays.

The detection system 14 includes the detector 103 and a data acquisition system (DAS) 104. The detector 103 detects the X-rays generated from the X-ray tube 101. The detector 103 is equipped with a plurality of detection elements arrayed two-dimensionally. Each detection element detects the X-rays generated from the X-ray tube 101 and generates an electrical signal (current signal) corresponding to the intensity of the detected X-rays.

The generated electrical signal is supplied to the DAS 104. The DAS 104 includes an amplifier 104A, an A/D converter 104B, and a control panel 104C. The DAS 104 reads out electrical signals via the detector 103 and acquires the readout electrical signals, via the control panel 104C. The gantry control transmission circuitry 15 controls the high voltage generator 120, the attenuator 821, the collimator 822, and the control panel 104 to execute X-ray imaging.

The console 20 includes pre-processing circuitry 21, Image-combining circuitry 22, a display 23, an operation device 24, data storage 25, and system control circuitry 26.

The pre-processing circuitry 21 executes pre-processing, such as logarithmic conversion and sensitivity correction for raw data supplied from the DAS 104, via the gantry control transmission circuitry 15. The data for which the pre-processing has been executed is called projection data.

The image-combining circuitry 22 can perform the image combining methods described herein, including methods 100, 200, 300, and 400.

The display 23 displays the image generated by the image-combining circuitry 22.

The operation circuitry 24 accepts various types of commands and information inputs from a user, via an input device.

The data storage (memory) 25 stores the raw data and various types of data, such as projection data and images. In addition, the data storage 25 stores control programs for the X-ray apparatus, and control programs for performing the image-combining methods described herein.

The system control circuitry 26 functions as the main circuitry of the X-ray apparatus. The system control circuitry 26 reads out control programs stored in the data storage 25 and loads the programs into the memory. The system control circuitry 26 controls the respective circuitry in the X-ray apparatus in accordance with the loaded control programs.

Figure 9:
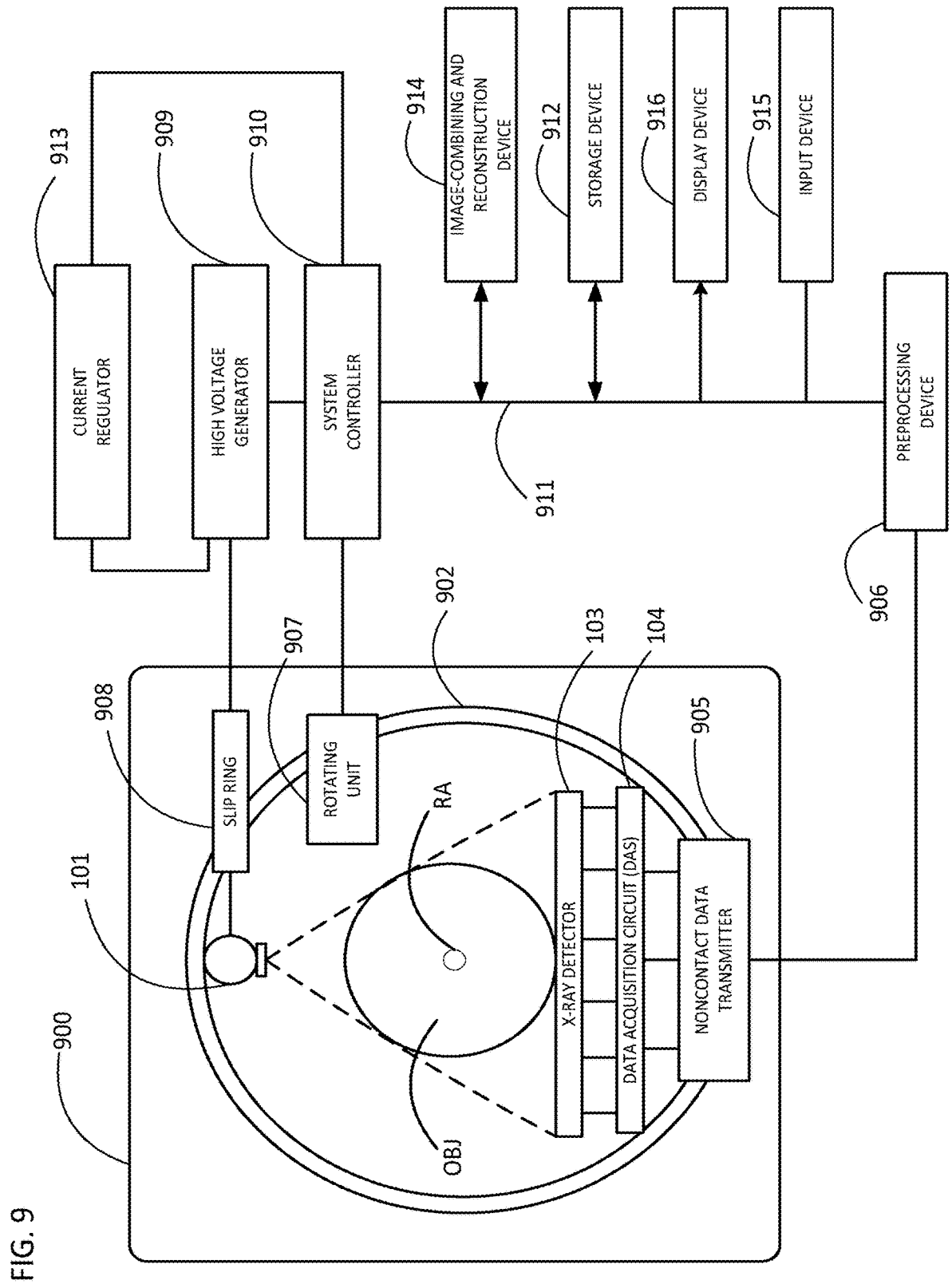
FIG. 9 is a block diagram of an example of a CT scanner apparatus, according to one embodiment.

FIG. 9 is a block diagram of an exemplary CT scanner apparatus that can be used with methods described herein, such as method 300, for example. As shown in FIG. 9, a radiography gantry 100 is illustrated from an axial view and further includes an X-ray tube 101, an annular frame 902, and a multi-row or two-dimensional-array-type X-ray detector 103. The X-ray tube 101 and X-ray detector 103 are diametrically mounted across an object OBJ on the annular frame 902, which is rotatably supported around a rotation axis RA. A rotating unit 907 rotates the annular frame 902 at a speed, such as 0.4 sec/rotation, while the object OBJ is being moved along the axis RA into or out of the illustrated page.

X-ray computed tomography apparatuses include various types of apparatuses. In one example, a rotate/rotate-type apparatus has an X-ray tube and X-ray detector which rotate together around an object to be examined. In a second example, a stationary/rotate-type apparatus has many detection elements which are arrayed in the form of a ring or plane, and only an X-ray tube rotates around an object to be examined. The present disclosures can be applied to either type. With reference to FIG. 9, the rotate/rotate type is illustrated.

The multi-slice X-ray CT apparatus further includes a high voltage generator 909 that generates a tube voltage applied to the X-ray tube 101 through a slip ring 908 so that the X-ray tube 101 generates X-rays. The X-rays are emitted towards the object OBJ, whose cross-sectional area is represented by a circle. The X-ray detector 103 is located at an opposite side from the X-ray tube 101 across the object OBJ for detecting the emitted X-rays that have transmitted through the object OBJ. The X-ray detector 103 further includes individual detector elements or units.

The CT apparatus further includes other devices for processing the detected signals from X-ray detector 103. A data acquisition circuit or a Data Acquisition System (DAS) 104 converts a signal output from the X-ray detector 103 for each channel into a voltage signal, amplifies the signal, and further converts the signal into a digital signal. The X-ray detector 103 and the DAS 104 are configured to handle a predetermined total number of projections per rotation (TPPR). Examples of TPPRs include, but are not limited to 900 TPPR, 900-1800 TPPR, and 900-3600 TPPR.

The above-described data is sent to a pre-processing device 906, which is housed in a console outside the radiography gantry 900 through a non-contact data transmitter 905. The pre-processing device 906 performs certain corrections, such as sensitivity correction on the raw data. A storage device 912 stores the resultant data, which is also called projection data at a stage immediately before reconstruction processing. The storage device 912 is connected to a system controller 910 through a data/control bus 911, together with a reconstruction device 914, input device 915, and display device 916. The system controller 910 controls a current regulator 913 that limits the current to a level sufficient for driving the CT system.

The detectors are rotated and/or fixed with respect to the patient among various generations of the CT scanner systems. In one implementation, the above-described CT system can be an example of a combined third-generation geometry and fourth-generation geometry system. In the third-generation system, the X-ray tube 101 and the X-ray detector 103 are diametrically mounted on the annular frame 902 and are rotated around the object OBJ as the annular frame 902 is rotated about the rotation axis RA. In the fourth-generation geometry system, the detectors are fixedly placed around the patient and an X-ray tube rotates around the patient. In an alternative embodiment, the radiography gantry 900 has multiple detectors arranged on the annular frame 902, which is supported by a C-arm and a stand.

The storage device 912 can store the measurement value representative of the irradiance of the X-rays at the X-ray detector unit 103. Further, the storage device 912 can store a dedicated program for executing a CT image reconstruction method and the image-combining methods discussed herein.

The reconstruction device 914 can execute the CT image reconstruction methods and the image-combining methods discussed herein. Further, reconstruction device 914 can execute pre-reconstruction image processing such as volume rendering processing and image difference processing as needed. The pre-reconstruction processing of the projection data performed by the pre-processing device 906 can include correcting for detector calibrations, detector nonlinearities, polar effects, noise balancing, and material decomposition.

Post-reconstruction processing performed by the reconstruction device 914 can include filtering and smoothing the image, volume rendering processing, and image difference processing as needed. The image reconstruction process can be performed using filtered back projection, iterative image reconstruction methods, or stochastic image reconstruction methods. The reconstruction device 914 can use the storage device 912 to store projection data, reconstructed images, calibration data and parameters, and computer programs, for example.

The reconstruction device 914 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the storage device 912 can be non-volatile, such as ROM, EPROM, EEPROM or FLASH memory. The storage device 912 can also be volatile, such as static or dynamic RAM. A processor, such as a microcontroller or microprocessor, and storage device 912 can be provided to manage the electronic memory, as well as the interaction between the FPGA or CPLD and the storage device 912.

Alternatively, the CPU in the reconstruction device 914 can execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor.

In one implementation, the reconstructed images can be displayed on a display device 916. The display device 916 can be an LCD display, CRT display, plasma display, OLED, LED, or any other display known in the art. The storage device 912 can be a hard disk drive, CD-ROM drive, DVD drive, FLASH drive, RAM, ROM or any other electronic storage known in the art.

Figure 11:
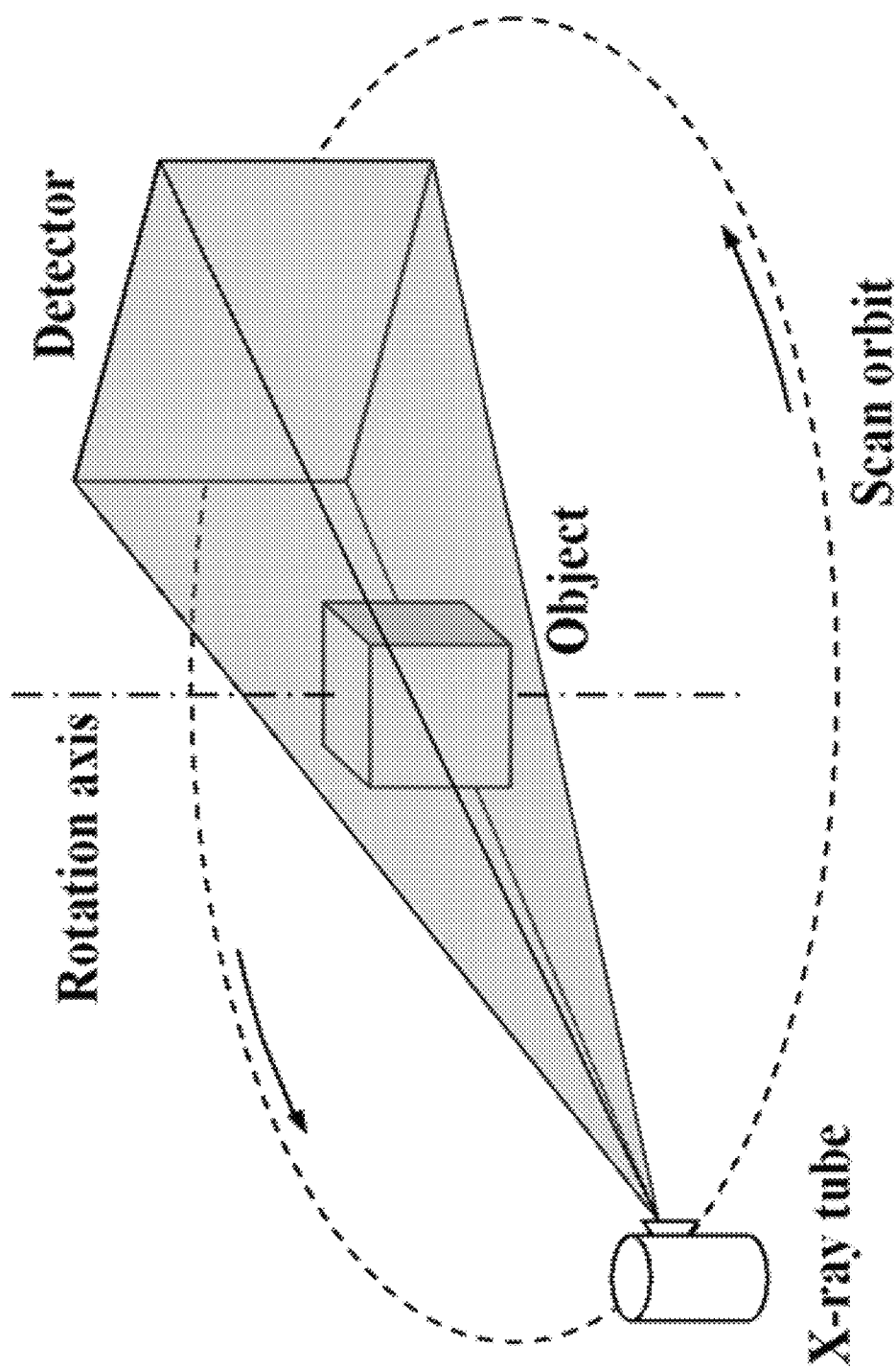
FIG. 11 is a block diagram of an exemplary cone beam CT scanner apparatus, according to one embodiment.

FIG. 11 is a block diagram of an exemplary cone beam CT scanner apparatus (also known as a CBCT scanner) that can be used with method described herein, such as methods 300 and 400. The CBCT scanner rotates about an object, such as a patient. The region of interest is centered in the field of view of the cone beam. A single rotation over the region of interest acquires a volumetric data set, which is collected and reconstructed to produce a digital volume. The digital volume includes three-dimensional voxels of anatomical data, which can be manipulated and visualized, via processing circuitry and associated specialized software.

A hardware description of a computing device 1000 according to exemplary embodiments is described with reference to FIG. 10. Computing device 1000 includes the system controller 110, the reconstruction device 114, the storage device 112, the display device 116, the input device 115, and/or the preprocessing device 906 illustrated in FIG. 9, either as a combined device or as one or more individual devices. In addition, the gantry control transmitting circuitry 15, the pre-processing circuitry 21, the reconstructing circuitry 22, and the system control circuitry 26 illustrated in FIG. 8.

Computing device 1000 includes a CPU 1001 which performs the methods described herein. For example, the computing device 1000 can perform one of methods 100, 200, 300, and 400 when the projection data have been obtained previously and stored on the memory 1002 or the disk 1004 of the computing device 1000. The projection data and instructions can be stored in memory 1002. These processes and instructions can also be stored on a storage medium disk 1004 such as a hard disk drive (HDD) or portable storage medium or can be stored remotely. Further, the claimed features are not limited by the form of the computer-readable media on which the instructions of the process are stored. For example, the instructions can be stored on CDs, DVDs, in FLASH memory, RAM, ROM, PROM, EPROM, EEPROM, hard disk or any other information processing device with which the computing device 1000 communicates, such as a server or computer.

The claimed features can be provided as a utility application, background daemon, or component of an operating system, or combination thereof, executing in conjunction with CPU 1001 and an operating system such as Microsoft Windows 7, UNIX, Solaris, LINUX, Apple MAC-OS and other systems known to those skilled in the art.

The computing device 1000 can be realized by various circuitry elements. For example, CPU 1001 can be a Xenon or Core processor from Intel of America or an Opteron processor from AMD of America, or can be other processor types that would be recognized by one of ordinary skill in the art. Alternatively, the CPU 1001 can be implemented on an FPGA, ASIC, PLD or using discrete logic circuits, as one of ordinary skill in the art would recognize. Further, CPU 1001 can be implemented as multiple processors cooperatively working in parallel to perform the instructions of the inventive processes described above and below.

Figure 10:
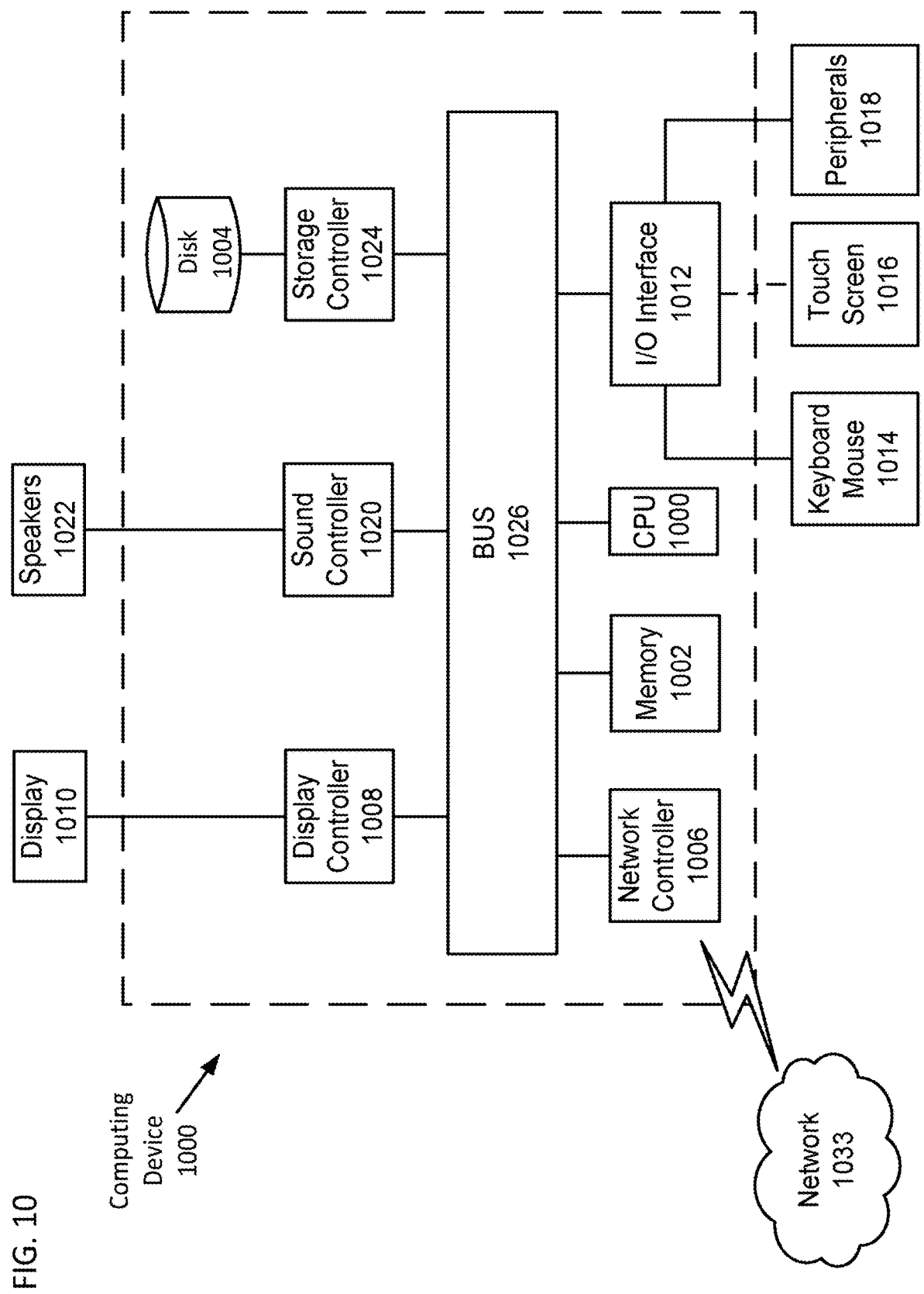
FIG. 10 is a block diagram of a hardware description of a computing device for performing image combining, according to one embodiment.

The computing device 1000 in FIG. 10 also includes a network controller 1006, such as an Intel Ethernet PRO network interface card from Intel Corporation of America, for interfacing with network 1033. As can be appreciated, the network 1033 can be a public network, such as the Internet, or a private network such as an LAN or WAN network, or any combination thereof and can also include PSTN or ISDN sub-networks. The network 1033 can also be wired, such as an Ethernet network, or can be wireless such as a cellular network including EDGE, 3G and 4G wireless cellular systems. The wireless network can also be WiFi, Bluetooth, or any other wireless form of communication that is known.

The computing device 1000 further includes a display controller 1008, such as a NVIDIA GeForce GTX or Quadro graphics adaptor from NVIDIA Corporation of America for interfacing with display 1010, such as a Hewlett Packard HPL2445w LCD monitor. A general purpose I/O interface 1012 interfaces with a keyboard and/or mouse 1014 as well as a touch screen panel 1016 on or separate from display 1010.

General purpose I/O interface 1012 also connects to a variety of peripherals 1018 including printers and scanners, such as an OFFICEJET or DESKJET from Hewlett Packard. A sound controller 1020 is also provided in the computing device 1000, such as SOUNDBLASTER X-FI TITANIUM from Creative, to interface with speakers/microphone 1022 thereby providing and/or receiving sounds and/or music.

The general purpose storage controller 1024 connects the storage medium disk 104 with communication bus 1026, which can be an ISA, EISA, VESA, PCI, or similar, for interconnecting all of the components of the computing device 1000. A description of the general features and functionality of the display 1010, keyboard and/or mouse 1014, as well as the display controller 1008, storage controller 1024, network controller 106, sound controller 1020, and general purpose I/O interface 1012 is omitted herein for brevity.

FIG. 12 is an exemplary lookup table 1200 used to choose the kernel function (i.e., the point-spread function under the particular conditions). A given X-ray system has certain inherent properties and parameters, including the current milli-ampere—(mA) and peak kilovoltage (kVp) applied at the X-ray source, and the focal-spot size (FS). These parameters can be used as indices into the lookup table 1200 to determine a resulting kernel function. Alternatively, when a resolution corresponding to a particular kernel function or subset of kernel functions is desired, the lookup table 1200 can be used to determine the current milli-ampere—(mA) and peak kilovoltage (kVp) applied at the X-ray source, and the focal-spot size (FS) that can achieve the desired spatial resolution. Further, the choice of current milli-ampere—(mA) and peak kilovoltage (kVp) applied at the X-ray source, and the focal-spot size (FS) can be further guided by a desired exposure. In certain implementations, tradeoffs might be made to come as close as possible to the desired resolution and exposure.

The mAs is a product of the tube current and an exposure time, which is a primary controlling factor of radiographic intensity.

The kVp is the maximum voltage applied across an X-ray tube. It determines the kinetic energy of the electrons accelerated in the X-ray tube and the peak energy of the X-ray emission spectrum. The kVp also affects the radiographic contrast indirectly. As the energy of the stream of electrons in the X-ray tube increases, the higher energy X-ray photons created from the higher energy electrons are more likely to penetrate the cells of the body and reach the image receptor. This results in increased radiographic signal magnitude. However, scattered X-rays also contribute to increased radiographic signal magnitude, wherein the higher the kVp of the beam, the more scatter is produced.

The focal-spot size and distribution can vary for each X-ray apparatus. The focal-spot size and distribution depend on the aperture size and distribution of the electron beam source, the wavelengths of the ionizing radiation spectrum, and the focal length. An X-ray apparatus can be configured with different focal-spot size s and distributions, depending on the desired application. In one embodiment given for illustrative purposes only, small, medium, and large focal-spot size s are used in the lookup table 1200. However, other naming conventions and numbers of focal-spot size s are contemplated by embodiments described herein.

The variables FS, kVp, and mA are used in the lookup table 1200 of FIG. 12. However, other variables pertinent to a particular X-ray system can be used. In FIG. 12, three values for each of the variables of FS, kVp, and mA have been used for ease of illustration. However, more or fewer than three values for any one of the variables are contemplated by embodiments described herein.

In certain implantations, the focal spots sizes, beam filter and kVp can be selected to obtain predefined exposures and resolutions in accordance with various clinical or research applications of the imaging system. For example, various protocols can be used for setting the relative and absolute values of the different sizes of focal spots for a given set of images. Also, the application can influence the ratio between the large and small focal-spot images in the combined image (i.e., the image ratio). The choice of image ratio will also depend on the nature of procedure and application. For applications in which high resolution is not a prerequisite and/or if low imaged object exhibit the properties of low contrast object coupled with large features, then high SNR will play a more prominent role in determining the image quality, making a choice of a greater contribution from the large focal-spot image relative to the small focal-spot image more optimal. Alternatively or even in combination, the parameters of the respective the large and small focal-spot images can be adjusted to increase exposure at the cost of lower resolution to improve image quality in the case of low contrast and large features.

On the other hand, for the case of high contrast and or fine features, the above processes can be reversed, as would be understood to a person of ordinary skill in the art. For example, if a stent strut is being imaged, the contribution from small focal spot could be weighted more heavily.

Further, it is contemplated that any number of images corresponding to different X-ray source parameters and focal-spot sizes can be combined to generate the combined image, as would be understood to a person of ordinary skill in the art.

The foregoing discussion discloses and describes merely exemplary embodiments of the present disclosure. As will be understood by those skilled in the art, the present disclosure may be embodied in other specific forms without departing from the spirit or essential characteristics thereof. Accordingly, the present disclosure is intended to be illustrative, but not limiting of the scope of the disclosure, including the claims. The disclosure, including any readily discernible variants of the teachings herein, defines in part, the scope of the foregoing claim terminology such that no inventive subject matter is dedicated to the public.

The invention claimed is:

1. A radiography apparatus, comprising:
processing circuitry configured to
obtain a first X-ray image of an object, the first X-ray image representing an attenuation of an intensity of X-ray radiation detected at a plurality of detectors, and corresponding to a first focal-spot size of an X-ray source generating the X-ray radiation,
obtain a second X-ray image of the object, the second X-ray image representing the attenuation of the intensity of X-ray radiation detected at the plurality of detectors, and corresponding to a second focal-spot size of the X-ray source, wherein the second focal-spot size is larger than the first focal-spot size,
combine the first X-ray image with the second X-ray image to generate a combined X-ray image, wherein a resolution of the combined image is finer than a resolution of the second X-ray image and a signal-to-noise ratio of the combined image is greater than a signal-to-noise ratio of the first X-ray image,
determine a change region within the first X-ray image, the second X-ray image, and the combined image, corresponding to spatial variations in the first X-ray image and the second X-ray image, and
determine a uniform region within the first X-ray image, the second X-ray image, and the combined image, corresponding to an absence of the spatial variations in the first X-ray image and the second X-ray image, wherein
the combining of the first X-ray image with the second X-ray image to generate the combined X-ray image includes superimposing the first X-ray image with the second X-ray image such that, within the uniform region, the combined X-ray image predominantly derives from the second X-ray image, and, within the change region, the combined X-ray image predominantly derives from the first X-ray image.

2. The radiography apparatus of claim 1, wherein the processing circuitry is further configured to
determine a high-frequency image by filtering the first X-ray image using a first filter, which has a high-frequency pass-band that passes high-frequency components and has a first frequency cutoff, and
determine a low-frequency image by filtering the second X-ray image using a second filter, which has a low-frequency pass-band that passes low-frequency components and has a second frequency cutoff, wherein
the combining of the first X-ray image with the second X-ray image to generate the combined X-ray image includes superimposing the low-frequency image with the high-frequency image.

3. The radiography apparatus of claim 2, wherein the processing circuitry is further configured to
determine the high-frequency image using the first frequency cutoff, which corresponds to a resolution of the second X-ray image and is determined using the second focal-spot size, and
determine the low-frequency image using the second frequency cutoff, which corresponds to the first frequency cutoff of the high-frequency image.

4. The radiography apparatus of claim 3, wherein the determining of the high-frequency image further includes filtering using the first filter, which is a band-pass filter, the first filter having a third frequency cutoff that is higher than the first frequency cutoff and corresponds to a resolution of the first X-ray image, which is determined using the first focal-spot size.

5. The radiography apparatus of claim 1, wherein the processing circuitry is further configured to
determine a low-frequency image from the second X-ray image using low-frequency components of a wavelet transformation of the second X-ray image, and
determine a high-frequency image from the first X-ray image using high-frequency components of a wavelet transformation of the first X-ray image, wherein
the combining of the first X-ray image with the second X-ray image to generate the combined X-ray image includes superimposing the low-frequency image with the high-frequency image.

6. The radiography apparatus of claim 1, wherein the processing circuitry is further configured to
determine a point-spread function of the first X-ray image using a magnification determined using a ratio of a source-to-imager distance (SID) to an source-to-object distance (SOD), and using the first focal-spot size and a distance between detector elements of the plurality of detectors, and
determine a point-spread function of the second X-ray image using the magnification, and using the second focal-spot size and the distance between detector elements of the plurality of detectors.

7. The radiography apparatus of claim 1, wherein the processing circuitry is further configured to
determine the first focal-spot size using a first tube current and a first tube voltage of the X-ray source used to obtain the first X-ray image, and
determine the second focal-spot size using a second tube current and a second tube voltage of the X-ray source used to obtain the second X-ray image.

8. The radiography apparatus of claim 1, wherein the processing circuitry is further configured to
obtain first computed tomography (CT) scan data of the object using the first focal-spot size, the first CT scan data including the first X-ray image,
obtain second CT scan data of the object using the first focal-spot size, the second CT scan data including the second X-ray image,
reconstruct a CT image from one of the first CT scan data and the second CT scan data,
determine a change region of the CT image corresponding to spatial variations in the CT image, and forward-project an image of the change region to generate a projected change region, and
determine a uniform region of the CT image corresponding to an absence of the spatial variations in the CT image, and forward-project an image of the uniform region to generate a projected uniform region, wherein
the combining of the first X-ray image with the second X-ray image to generate the combined X-ray image includes superimposing the first X-ray image with the second X-ray image such that, within the projected uniform region, the combined X-ray image predominantly derives from the second X-ray image, and, within the projected change region, the combined X-ray image predominantly derives from the first X-ray image.

9. The radiography apparatus of claim 1, wherein the processing circuitry is further configured to
perform material decomposition on one of the first X-ray image and the second X-ray image to generate material-component images,
determine a change region corresponding to spatial variations in relative material concentrations among the material-component images, and
determine a uniform region corresponding an absence of the spatial variations in the relative material concentrations among the material-component images, wherein
the combining of the first X-ray image with the second X-ray image to generate the combined X-ray image includes superimposing the first X-ray image with the second X-ray image such that the uniform region in the combined X-ray image predominantly derives from the second X-ray image and the change region in the combined X-ray image predominantly derives from the first X-ray image.

10. The radiography apparatus of claim 1, wherein the processing circuitry is further configured to determine the change region and the uniform region by
subtracting the first-X-ray image from the second X-ray image to generate a difference image,
perform a wavelet transformation on the difference image to generate wavelet components,
determine the change region as corresponding to the wavelet components exceeding a first threshold, and
determine the uniform region as corresponding to the wavelet components less than a second threshold.

11. The radiography apparatus of claim 1, wherein the processing circuitry is further configured to determine the change region using an edge-detection method.

12. The radiography apparatus of claim 1, wherein the processing circuitry is further configured to
obtain the first X-ray image and the second X-ray image by respectively reconstructing first projection data and second projection data, wherein
the first projection data and the second projection data are generated using one of an single-scan imaging method using a single scan acquiring projection images at a series of projection angles, and the respective projection images alternate between being acquired using the first focal-spot size and the second focal-spot size, and a multi-scan imaging method using respective scans each acquiring respective projection images at the projection angles using no more than one of the first focal-spot size and the second focal-spot size per scan.

13. The radiography apparatus of claim 1, wherein the processing circuitry is further configured to
determine the first focal-spot size of the X-ray source by selecting a first beam filter of the X-ray source and by selecting a first kVp value of the X-ray source, and
determine the second focal-spot size of the X-ray source by selecting a second beam filter of the X-ray source and by selecting a second kVp value of the X-ray source.

14. The radiography apparatus of claim 1, wherein the processing circuitry is further configured to
adjust the first focal-spot size to a smaller size for applications in accordance with a signal to increase the resolution of the combined image, and
adjust the second focal-spot size to increase an exposure corresponding to the second X-ray image in accordance with a signal to increase the signal-to-noise ratio of the combined image.

15. The radiography apparatus of claim 1, wherein the processing circuitry is further configured to
obtain at least one additional X-ray image of the object, the at least one additional X-ray image respectively representing the attenuation of the intensity of the X-ray radiation detected at the plurality of detectors, and respectively corresponding to at least one additional focal-spot size of the X-ray source generating the X-ray radiation, the at least one additional focal-spot size being unequal to the first focal-spot size and the second focal-spot size, and the combining of the first X-ray image with the second X-ray image to generate the combined X-ray image further including combining the least one additional X-ray image with the first X-ray image and the second X-ray image.

16. A radiography apparatus, comprising:
processing circuitry configured to
obtain a first X-ray image of an object, the first X-ray image representing an attenuation of an intensity of X-ray radiation detected at a plurality of detectors, and corresponding to a first focal-spot size of an X-ray source generating the X-ray radiation,
obtain a second X-ray image of the object, the second X-ray image representing the attenuation of the intensity of X-ray radiation detected at the plurality of detectors, and corresponding to a second focal-spot size of the X-ray source, wherein the second focal-spot size is larger than the first focal-spot size,
combine the first X-ray image with the second X-ray image to generate a combined X-ray image, wherein a resolution of the combined image is finer than a resolution of the second X-ray image and a signal-to-noise ratio of the combined image is greater than a signal-to-noise ratio of the first X-ray image,
determine a high-frequency image by filtering the first X-ray image using a first filter, which has a high-frequency pass-band that passes high-frequency components and has a first frequency cutoff, and
determine a low-frequency image by filtering the second X-ray image using a second filter, which has a low-frequency pass-band that passes low-frequency components and has a second frequency cutoff, wherein
the combining of the first X-ray image with the second X-ray image to generate the combined X-ray image includes superimposing the low-frequency image with the high-frequency image.

17. The radiography apparatus of claim 16, further comprising:
a radiation source configured to generate the X-ray radiation; and
a radiation detector configured to receive the X-ray radiation from the radiation source.

18. A radiography apparatus, comprising:
processing circuitry configured to
obtain a first X-ray image of an object, the first X-ray image representing an attenuation of an intensity of X-ray radiation detected at a plurality of detectors, and corresponding to a first focal-spot size of an X-ray source generating the X-ray radiation,
obtain a second X-ray image of the object, the second X-ray image representing the attenuation of the intensity of X-ray radiation detected at the plurality of detectors, and corresponding to a second focal-spot size of the X-ray source, wherein the second focal-spot size is larger than the first focal-spot size,
combine the first X-ray image with the second X-ray image to generate a combined X-ray image, wherein a resolution of the combined image is finer than a resolution of the second X-ray image and a signal-to-noise ratio of the combined image is greater than a signal-to-noise ratio of the first X-ray image,
determine a low-frequency image from the second X-ray image using low-frequency components of a wavelet transformation of the second X-ray image, and
determine a high-frequency image from the first X-ray image using high-frequency components of a wavelet transformation of the first X-ray image, wherein
the combining of the first X-ray image with the second X-ray image to generate the combined X-ray image includes superimposing the low-frequency image with the high-frequency image.

19. The radiography apparatus of claim 18, further comprising:
a radiation source configured to generate the X-ray radiation; and
a radiation detector configured to receive the X-ray radiation from the radiation source.

20. A radiography apparatus, comprising:
processing circuitry configured to
obtain a first X-ray image of an object, the first X-ray image representing an attenuation of an intensity of X-ray radiation detected at a plurality of detectors, and corresponding to a first focal-spot size of an X-ray source generating the X-ray radiation,
obtain a second X-ray image of the object, the second X-ray image representing the attenuation of the intensity of X-ray radiation detected at the plurality of detectors, and corresponding to a second focal-spot size of the X-ray source, wherein the second focal-spot size is larger than the first focal-spot size,
combine the first X-ray image with the second X-ray image to generate a combined X-ray image, wherein a resolution of the combined image is finer than a resolution of the second X-ray image and a signal-to-noise ratio of the combined image is greater than a signal-to-noise ratio of the first X-ray image,
determine a point-spread function of the first X-ray image using a magnification determined using a ratio of a source-to-imager distance (SID) to an source-to-object distance (SOD), and using the first focal-spot size and a distance between detector elements of the plurality of detectors, and
determine a point-spread function of the second X-ray image using the magnification, and using the second focal-spot size and the distance between detector elements of the plurality of detectors.

21. The radiography apparatus of claim 20, further comprising:
a radiation source configured to generate the X-ray radiation; and
a radiation detector configured to receive the X-ray radiation from the radiation source.

* * * * *